United States Patent
Ma et al.

(10) Patent No.: US 11,040,126 B2
(45) Date of Patent: Jun. 22, 2021

(54) DEGRADABLE CORROSION-RESISTANT HIGH STRENGTH AND DUCTILITY MAGNESIUM ALLOY FOR BIOMEDICAL USE AND PREPARATION METHOD THEREFOR

(71) Applicant: AmsinoMed Medical Co., Ltd, Beijing (CN)

(72) Inventors: Guorui Ma, Beijing (CN); Xiaoyi Ma, Beijing (CN)

(73) Assignee: AmsinoMed Medical Co., Ltd, Beijing (CN)

( * ) Notice: Subject to any disclaimer, the term of this patent is extended or adjusted under 35 U.S.C. 154(b) by 127 days.

(21) Appl. No.: 16/312,261

(22) PCT Filed: Jun. 29, 2016

(86) PCT No.: PCT/CN2016/087575
§ 371 (c)(1),
(2) Date: Dec. 20, 2018

(87) PCT Pub. No.: WO2018/000219
PCT Pub. Date: Jan. 4, 2018

(65) Prior Publication Data
US 2019/0201590 A1    Jul. 4, 2019

(51) Int. Cl.
C22C 23/06 (2006.01)
A61L 31/02 (2006.01)
A61L 31/14 (2006.01)
C22C 23/00 (2006.01)

(52) U.S. Cl.
CPC ........... *A61L 31/022* (2013.01); *A61L 31/148* (2013.01); *A61L 2400/18* (2013.01); *C22C 23/00* (2013.01)

(58) Field of Classification Search
CPC .................. C22F 1/06; C22C 23/06
See application file for complete search history.

(56) References Cited

U.S. PATENT DOCUMENTS

2012/0070248 A1* 3/2012 Kuwabara ............... F16B 33/00
411/378

FOREIGN PATENT DOCUMENTS

| CN | 100998893 A | 7/2007 |
|---|---|---|
| CN | 101062427 A | 10/2007 |
| CN | 101288776 A | 10/2008 |
| CN | 101484599 A | 7/2009 |
| CN | 101629260 A | 1/2010 |
| CN | 101643872 A | 2/2010 |
| CN | 101837145 A | 9/2010 |
| CN | 101985714 A | 3/2011 |
| CN | 103184379 A | 7/2013 |
| CN | 103774017 A | 5/2014 |
| CN | 104164602 A | 11/2014 |
| CN | 104232972 A | 12/2014 |
| DE | 10 2012 108 089 A1 | 5/2014 |
| WO | WO 2011/160534 A1 | 12/2011 |

OTHER PUBLICATIONS

International Search Report, PCT/CN2016/087575 (dated Dec. 30, 2016).
International Preliminary Report on Patentability for PCT App. No. PCT/CN2016/08757 dated Jan. 10, 2019 (13 pages).
Written Opinion for PCT App. No. PCT/CN2016/087575 dated Dec. 30, 2016 (10 pages).
Extended European Search Report, App. No. 16906621.4, 8 pages (dated Jan. 18, 2019).

* cited by examiner

*Primary Examiner* — Jessee R Roe
(74) *Attorney, Agent, or Firm* — Foley & Lardner LLP

(57) ABSTRACT

The present disclosure provides a degradable corrosion-resistant high strength and ductility magnesium alloy for biomedical use and the preparation method therefor. With regard to a total weight of the magnesium alloy of 100%, the composition of components of the magnesium alloy comprises: 1.0 to 4.5% of Nd, 0.2 to 2.0% of Zn, 0 to 1.0% of Ca, 0 to 1.0% of Zr, and balance of Mg. The magnesium alloy is prepared by producing a magnesium alloy ingot by means of vacuum semi-continuous casting and according to the components and weight percentage thereof followed by solid solution treatment and extrusion. The degradable corrosion-resistant high strength and ductility magnesium alloy for biomedical use provided by the present disclosure has the advantages of being non-toxic and fully degradable, good corrosion resistance as well as high strength and ductility etc., and can be used for preparing a vascular stent.

17 Claims, No Drawings

DEGRADABLE CORROSION-RESISTANT HIGH STRENGTH AND DUCTILITY MAGNESIUM ALLOY FOR BIOMEDICAL USE AND PREPARATION METHOD THEREFOR

CROSS-REFERENCE TO RELATED APPLICATIONS

This application is a U.S. National Stage Application of International Application No. PCT/CN2016/087575, filed Jun. 29, 2016, which is incorporated herein by reference in its entirety.

TECHNICAL FIELD

The present invention relates to a degradable corrosion-resistant high strength and ductility magnesium alloy for biomedical use and the preparation method therefor, which pertains to the field of medical material preparation techniques.

BACKGROUND

At present, the vascular stents used clinically are mainly made of inert metal materials such as stainless steel, nickel-titanium alloys and cobalt-chromium alloys. The implantation of such stents in the human body can provide long-lasting mechanical support for the blood vessels at the lesion, avoid the elastic retraction of the blood vessels, and lower the restenosis rate of the blood vessels. However, a stent made of inert metal materials as a foreign body causes excessive hyperplasia of the intima of the blood vessels after implantation, which not only causes vascular restenosis and late thrombosis, but also requires long-term antiplatelet therapy. In recent years, the use of drug-eluting stents has reduced the restenosis rate of blood vessels to about 5%. However, upon completion of the drug release, the stent body permanently remains in the body. There is a great difference in mechanical properties between the stent as a foreign body and vascular tissues, which can cause chronic damage to the blood vessel and, at a later stage, atrophy of the middle vascular layers and intimal hyperplasia, and eventually lead to restenosis of the blood vessels. For pediatric patients, the implantation of a fixed-size stent will hinder the gradual enlargement of the blood vessel, and it is even more difficult to adapt to the needs of their growth and development. In view of the above reasons, the development of biodegradable vascular stents has become a hot research project in various countries.

There are two types of degradable vascular stents that have obtained registration certificates or entered clinical trials: one as degradable polymer stents, and the other as degradable magnesium alloy stents. Degradable polymer stents has problems of low mechanical properties, difficulty in processing, and in vivo degradation products that can easily cause inflammation and swelling. A large amount of clinical data shows that patients have a chance of up to 16% of developing advanced restenosis after implantation of a polymer stent. As compared to degradable polymer stents, degradable magnesium alloy stents mainly have the following advantages: (1) it can be completely degraded after being implanted into the human body. A magnesium alloy stent can be completely absorbed by the body generally within 4 months after implantation. The feature of complete degradability of magnesium alloy stents not only can improve the compliance and naturalness of the blood vessel to a certain extent, but can also re-introduce a stent at the same lesion site in a blood vessel without causing stent overlapping, which is especially suitable for the treatment of cardiovascular diseases in infants and young children. (2) Good biocompatibility. Since magnesium is an essential element for the human body to maintain normal physiological functions while the blood vessel stent has a minute size (a hollow tubular shape with a diameter of approximately 2 mm, a wall thickness of approximately 0.1 to 0.2 mm, and a length of approximately 15 mm) and release a small amount of metal ions in the degradation process, the small amount of magnesium ions released during the degradation of the magnesium alloy stent not only does not cause harm to the human body, but would rather supplement magnesium to the body, so as to meet the need in magnesium for normal physiological functions of the body. (3) Because the magnesium alloy stent can be completely absorbed by the body, non-invasive examination can be performed during follow-ups after stent implantation. (4) Appropriate support strength. Magnesium alloy as a vascular stent material does not have the problem of insufficient strength that polymer materials have, allowing the vascular stent to have an appropriate support strength.

However, the low standard electrode potential of magnesium alloys (−2.36V SCE) leads to poor corrosion resistance, and corrosion is particularly severe in a corrosive environment in which chloride ions (CO are present or when the medium has a pH≤11.5. As bio-implantation materials, magnesium alloys must strictly meet the necessary mechanical and morphological requirements during service, and therefore should not have a too fast rate of degradation by corrosion. The in vivo environment has a pH of around 7.4, with a large amount of chloride ions present in the body fluids, which, in addition to the complicated corrosive nature of the in vivo environment, may lead to change in the corrosion rate of magnesium alloys in the body. For these reasons, medical corrosion-resistant magnesium alloys have been developed, such as the medical corrosion-resistant magnesium alloy disclosed in CN101062427A and the medical high strength and toughness corrosion-resistant magnesium alloy disclosed in CN101288776A.

Another factor that limits the widespread use of magnesium alloys lies in its low plasticity at room temperature and the difficulty in deformation processing. This is because magnesium pertains to a metal of a densely packed hexagonal crystalline structure, with few independent slip systems at room temperature except the base slip. In view of the issue of poor plasticity at room temperature of magnesium alloys, high strength magnesium alloys have been developed, such as the high strength and high plasticity magnesium alloy and the preparation method thereof disclosed in CN101643872A, and the high plasticity magnesium alloy and the preparation method thereof disclosed in CN101985714A.

Most of the magnesium alloys in the above patent documents contain Al element and heavy rare earth elements (Y, Gd, etc.). It is well-known that the Al element may cause some degenerative neurological diseases such as dialysis encephalopathy syndrome, senile dementia, and is considered to be a harmful neurotoxic element to the human body. Although Y, Gd and other heavy rare earth elements can increase the strength and corrosion resistance of magnesium alloys, their biological effects are not yet clear and it is generally believed that the accumulation of heavy rare earth elements in the body manifest a toxic action.

CN101629260A discloses a medical absorbable Mg—Zn—Mn—Ca magnesium alloy. The components and weight percentages in the magnesium alloy are: 1.0 to 5.0% of Zn, 0.2 to 2.0% of Mn, 0.1 to 3.0% of Ca, and the balance of Mg. The magnesium alloy has fair biocompatibility and mechanical properties and can be made into implantable devices such as bone nails and bone plates. However, the magnesium alloy cannot be used for the preparation of vascular stents, primarily for the reasons including: (1) compromised corrosion-resistant performance of the magnesium alloy due to the addition of the Mn element with a relatively high content, resulting in too fast degradation rate and frequent occurring of local uneven degradation; and (2) poor ductility of the alloy and difficulty in plastic processing, making it difficult to achieve secondary molding.

CN103184379A discloses a biodegradable Mg—Gd—Zn—Ag—Zr type magnesium alloy and the preparation method thereof. The components and weight percentages of the magnesium alloy are: 5 to 10% of Gd, 0.5 to 3% of Zn, 0.1 to 1% of Ag, 0.1 to 1% of Zr, and the balance of Mg. The magnesium alloy can be used as an implant material with low degradation rate and uniform corrosion. However, the deficiency of this magnesium alloy lies in the relatively high content of the heavy rare earth element Gd in the components ($\geq 5\%$), whereas the Gd element is considered toxic and disadvantageous in improving the biocompatibility of the alloy. In addition, the magnesium alloy contains the expensive Ag element and requires strict preservation and smelting conditions, thereby increasing the cost.

In summary, it is urgent to develop a novel biomedical magnesium alloy that is non-toxic, fully degradable, has good corrosion resistance, high strength and ductility, and explores the possibility of its application in intravascular stents.

SUMMARY

To solve the above technical problems, an object of the present disclosure is to provide a degradable corrosion-resistant high strength and ductility magnesium alloy for biomedical use and a preparation method thereof. The magnesium alloy has the advantages of being non-toxic and fully degradable, good corrosion resistance as well as high strength and toughness and the like, and can be used for preparing a vascular stent.

In order to achieve the above object, the present disclosure first provides a degradable corrosion-resistant high strength and ductility magnesium alloy for biomedical use, wherein the composition of components of the magnesium alloy comprises 1.0 to 4.5% of Nd, 0.2 to 2.0% of Zn, 0 to 1.0% of Ca, 0 to 1.0% of Zr, and balance of Mg, with regard to a total weight of the magnesium alloy of 100%.

According to a preferred embodiment, the composition of the components comprises 1.5 to 3.5% of Nd, 0.1 to 1.0% of Zn, 0.1 to 1.0% of Ca, 0.2 to 1.0% of Zr, and balance of Mg, with regard to a total weight of the degradable corrosion-resistant high strength and ductility magnesium alloy for biomedical use of 100%.

According to a more preferred embodiment, the composition of components of the magnesium alloy comprises 1.5 to 2.5% of Nd, 0.4 to 0.8% of Zn, 0.4 to 0.6% of Ca, 0.4 to 0.8% of Zr, and balance of Mg, with regard to a total weight of the degradable corrosion-resistant high strength and ductility magnesium alloy for biomedical use of 100%. The contents of components of this preferred magnesium alloy enable better overall mechanical performance and biological corrosion performance to be achieved thereby.

In the above degradable corrosion-resistant high strength and ductility magnesium alloy for biomedical use, preferably, with regard to a total weight of the magnesium alloy of 100%, the total amount of inclusion elements other than Mg, Nd, Zn, Ca, and Zr contained in the magnesium alloy is 0.05% or less. By strictly controlling the contents of Fe, Cu, Ni and other impurities, the magnesium alloy may be conferred with better overall mechanical performance and biological corrosion performance.

According to a specific embodiment, preferably, the above degradable corrosion-resistant high strength and ductility magnesium alloy for biomedical use is prepared by at least the step of: preparing a magnesium alloy ingot according to the components and weight percentage in the degradable corrosion-resistant high strength and ductility magnesium alloy for biomedical use, wherein the raw materials used comprise at least: pure Zn, a Mg—Nd master alloy, and pure magnesium. More preferably, the raw materials used further comprise pure Ca and/or a Mg—Zr master alloy. Further preferably, the pure Zn used has a purity of 99.99 wt % or more, the pure Ca used has a purity of 99.99 wt % or more, the Mg—Nd master alloy used is a Mg-30 wt % Nd master alloy, the Mg—Zr master alloy used is a Mg-30 wt % Zr master alloy, and the pure magnesium used has a purity of 99.99 wt % or more. In addition, the resultant magnesium alloy ingot may have a size of Φ110 to 150 mm in diameter and 2200 to 2600 mm in length.

According to a specific embodiment, preferably, the above preparation of the degradable corrosion-resistant high strength and ductility magnesium alloy for biomedical use further comprises: cutting the resultant magnesium alloy ingot to a certain length, and subjecting it to solid solution treatment before extruding, so as to obtain the degradable corrosion-resistant high strength and ductility magnesium alloy for biomedical use. Here, more preferably, the temperature of the solid solution treatment is 480 to 540° C., the duration of the solid solution treatment is 8 to 12 hours, the extrusion is performed at an extruding ratio of 5 to 30 in an environment at 280 to 420° C., and the degradable corrosion-resistant high strength and ductility magnesium alloy for biomedical use is obtained after the extrusion as a round rod with a diameter of Φ20 to 40 mm.

The roles of each element in the degradable corrosion-resistant high strength and ductility magnesium alloy for biomedical use are as follows, respectively:

The incorporation of Nd brings about an excellent aging precipitation strengthening and solid solution strengthening effect to the magnesium alloy, because Nd forms a strengthening phase Mg2Nd in the magnesium alloy and this strengthening phase can increase the strength and plasticity of the alloy. Also, the incorporation of Nd can greatly increase the electrode potential of the magnesium alloy substrate and reduce the difference in electric potential between the galvanic corrosion of the substrate and the second phase, thereby significantly improving the corrosion resistance of the magnesium alloy. In addition, Nd belongs to light rare earth elements and has good biological safety.

Zn is an element that has significant influence on cell growth and development and is a necessary micronutrient element in the human body. Zn can enhance the immunity in the human body and maintain growth and development in the body. In vitro experiments showed that Zn can maintain the barrier function of vascular endothelial cell membranes. In view of the mechanical properties of magnesium alloys, Zn has a 6.2% solid solubility in the magnesium alloy, and plays a role in the solid solution strengthening of the magnesium alloy, while effectively promoting the occurrence of non-basal surface slipping in the magnesium alloy at room temperature and improving the plastic processability of the magnesium alloy. Zn is another highly effective alloying element other than Al. In addition, when the Zn content is less than 2%, the local corrosion in the magnesium alloy tends to be reduced, effectively improving the corrosion resistance of the magnesium alloy.

The inclusion of Ca can refine the grains in the magnesium alloy, which is effective in strengthening the fine grains, and significantly improve the moldability and strength of the magnesium alloy. Ca can also suppress the oxidation of the molten metal during the smelting of the magnesium alloy and reduce internal defects in ingots. Ca can reduce the microbattery effect in a magnesium alloy and increase the corrosion resistance of the magnesium alloy. Meanwhile, Ca is also one of the most abundant elements in the human body, and about 99% of Ca is present in bone marrows and teeth in vivo, with the remaining primarily distributed in body fluids for participating in certain important enzyme reactions. Ca plays an important role in maintaining the normal contraction of the heart, neuromuscular excitability, coagulation, and normal secretion of endocrine hormones, as well as in maintenance of cell membrane integrity, and the like.

Zr has a strong solid solution strengthening effect and can significantly increase the strength of a magnesium alloy. Zr is also the most effective grain refining agent to date and has a strong grain refinement effect. In addition, Zr can significantly improve the tensile strength of the magnesium alloy at room temperature, improve corrosion resistance and reduce stress corrosion susceptibility. The addition of Zr into a Zn-containing magnesium alloy can reduce the tendency of embrittlement and temper embrittlement in the magnesium alloy, and can also reduce the contents of Fe, Al, Si, and other impurities in the alloy. Extensive domestic and overseas studies show that addition of Zr in a small amount into a magnesium alloy is not cytotoxic.

On the other hand, the present disclosure also provides a preparation method for the degradable corrosion-resistant high strength and ductility magnesium alloy for biomedical use described above, which comprises at least the step of: preparing a magnesium alloy ingot by means of vacuum semi-continuous casting and according to the components and weight percentage in the above-mentioned magnesium alloy, wherein the raw materials used comprise at least: pure Zn, a Mg—Nd master alloy and pure magnesium. Preferably, the raw materials used further comprise pure Ca and/or a Mg—Zr master alloy.

In the above preparation method, preferably, the pure Zn used has a purity of 99.99 wt % or more, the pure Ca used has a purity of 99.99 wt % or more, the Mg—Nd master alloy used is a Mg-30 wt % Nd master alloy, the Mg—Zr master alloy used is a Mg-30 wt % Zr master alloy, and the pure magnesium used has a purity of 99.99 wt % or more.

In the above preparation method, preferably, the vacuum semi-continuous casting comprises the following steps:

(1) the raw materials are melted in a vacuum melting furnace with a melt temperature controlled at 740 to 760° C. during melting, and after the raw materials are completely melted, an inert gas is introduced for stirring by gas in a vacuum environment with a stirring time of 30 to 45 min;

(2) after the stirring is completed, a mixed gas of $SF_6$ and $CO_2$ is introduced to the surface of the melt for protection while the temperature of the melt is raised to 760 to 780° C. and kept for 30 to 40 min, and then the temperature of the melt is lowered to 700 to 720° C. and the melt is allowed to stand for 90 to 120 min;

(3) casting is then carried out on a semi-continuous casting machine; during the semi-continuous casting process, a gas mixture of $SF_6$ and $CO_2$ is used for protection, the temperature of the melt in the vacuum melting furnace is controlled at 700 to 720° C., with the temperature of the melt in a crystallizer at 680 to 690° C. and a speed of ingot-drawing of 30 to 50 mm/min, and high pressure water-cooling is applied at 300 to 500 mm close to the crystallizer while air-cooling is applied at a lower region, thereby obtaining the magnesium alloy ingot.

In the above preparation method, preferably, the resultant magnesium alloy ingot has a size of Φ110 to 150 mm in diameter and 2200 to 2600 mm in length, and more preferably Φ120×2400 mm.

According to a specific embodiment, preferably, the above preparation method further comprises the following steps: cutting the obtained magnesium alloy ingot to a certain length, and subjecting it to solid solution treatment before extruding, so as to obtain the degradable corrosion-resistant high strength and ductility magnesium alloy for biomedical use. Here, more preferably, the temperature of the solid solution treatment is 480 to 540° C. (more preferably 520° C.), the duration of the solid solution treatment is 8 to 12 hours (more preferably 10 hours), the extrusion is performed at an extruding ratio of 5 to 30 (more preferably 25) in an environment at 280 to 420° C. (more preferably 330° C.), and the degradable corrosion-resistant high strength and ductility magnesium alloy for biomedical use is obtained after the extrusion as a round rod with a diameter of Φ20 to 40 mm (more preferably Φ25 mm).

Compared with the existing magnesium alloys for degradable vascular stents, the embodiments described herein have the following advantages:

1. The magnesium alloy of the present disclosure has an ideal corrosion resistance in vivo, and is uniformly eroded and degraded, so as to avoid premature failure of implant materials due to excessive local corrosion, thereby achieving an ideal supporting effect of a biodegradable material.

2. The present disclosure avoids the neurotoxicity caused by the Al element in Al-containing magnesium alloys in the composition design, and does not contain heavy rare earth elements (Y, Gd, etc.), while the selected alloying and microalloying elements are all non-cytotoxic within the proposed composition range and have good biocompatibility.

3. Under the same conditions in the preparation process, as compared to the existing magnesium alloys for degradable vascular stents, in the magnesium alloy of the present disclosure, the contents of alloying elements, especially rare earth elements, are lower than those in the WE43 alloy, which not only greatly improves the blood compatibility of the alloy, but also leads to less segregation of elements in the alloy, better corrosion resistance, remarkably reduced corrosion rate, and relatively uniform corrosion.

4. The quasi-crystalline phase occurring in the magnesium alloy prepared by the method of the present disclosure has excellent corrosion resistance, which greatly improves the corrosion resistance of the alloy. While the occurrence of the quasi-crystal phase significantly improves the corrosion resistance of magnesium alloys, the rigidity of the magnesium alloy can also be improved to some extent due to the special properties of quasicrystals, which solves the problem of insufficient rigidity of the magnesium alloy as a degradable blood vessel stent.

5. The magnesium alloy of the present disclosure has excellent comprehensive mechanical properties, excellent corrosion resistance and good biocompatibility after being processed by extrusion. The magnesium alloy prepared by the present disclosure has a tensile strength of 246 to 289

MPa, a yield strength of 207 to 232 MPa and an elongation rate of 25 to 34%, which meets the requirements for the mechanical properties of intravascular stent materials. Its corrosion rate in artificial plasma can reach 0.22 to 0.26 mm/year, which meets the requirement for the corrosion resistance of intravascular stent materials. In addition, the magnesium alloy has no obvious cytotoxicity and good blood compatibility, which meets the requirements for the biocompatibility of intravascular stent materials.

DETAILED DESCRIPTION

For clearer understanding of the technical features, objects, and advantages of the present disclosure, the technical solutions of the present disclosure will be described in detail below, but it should not be construed as limiting to the scope of the present disclosure.

Example 1

This example provides a degradable corrosion-resistant high strength and ductility magnesium alloy for biomedical use. The composition of the magnesium alloy comprises, with regard to a total weight of the magnesium alloy of 100%, 1.5% of Nd, 0.4% of Zn, 0.4% of Ca, 0.4% of Zr, and balance of Mg.

The magnesium alloy was prepared by the following steps:

(1) In a vacuum melting furnace, pure magnesium having a purity of 99.99 wt % or more, pure Zn having a purity of 99.99 wt % or more, pure Ca having a purity of 99.99 wt % or more, a Mg-30 wt % Nd master alloy and a Mg-30 wt % Zr master alloy were successively melted, and the melt temperature during melting was controlled at 740 to 760° C. After the raw materials were completely melted, argon gas was introduced to conduct gas stirring in a vacuum environment with a stirring time of 40 min.

(2) After the stirring was completed, a mixed gas of $SF_6$ and $CO_2$ (volume ratio of $SF_6:CO_2$ in this mixed gas being 1:100) was introduced to the surface of the melt for protection, and at the same time, the temperature of the melt was raised to 760 to 780° C. and kept for 30 min. After the high temperature insulation, the melting furnace was powered off, and the temperature of the melt was controlled at 700 to 720° C. and the melt was allowed to stand for 90 min.

(3) Subsequently, a copper crystallizer was used for the ingot casting on a semi-continuous casting machine. The magnesium alloy melt was introduced into a diverter plate placed in the core of the inner sleeve of the crystallizer, and was diverted by the diverter plate into the space formed by the metal inner sleeve and the dummy bar of the crystallizer. At the same time, the protective gas ring was opened to provide a mixed gas of $SF_6$ and $CO_2$ (volume ratio of $SF_6:CO_2$ in this mixed gas being 1:100) to the alloy melt for protection. During the semi-continuous casting process, the temperature of the melt in the vacuum melting furnace was controlled at 700 to 720° C., the temperature of the melt in the crystallizer was 680 to 690° C., and the speed of ingot-drawing was 40 mm/min. High pressure water-cooling was applied at 400 mm close to the crystallizer, and air-cooling was applied at a lower region.

(4) The Mg—Nd—Zn—Ca—Zr magnesium alloy semi-continuous ingot obtained from the casting had a size of Φ120×2400 mm. The ingot had an appearance free of cracks and shrinkage, with a smooth and clean surface, fine and uniform structures, and no solute segregation.

(5) The resultant Mg—Nd—Zn—Ca—Zr magnesium alloy ingot was cut to a certain length, subjected to solid solution treatment at 520° C. for 10 hours, and then extruded at 330° C. to form a round rod having a diameter of Φ25 mm, and thus the degradable corrosion-resistant high strength and ductility magnesium alloy for biomedical use was obtained.

The degradable corrosion-resistant high strength and ductility magnesium alloy for biomedical use had a tensile strength of 246 MPa, a yield strength of 207 MPa and an elongation of 34%, as well as good plasticity and mechanical properties. The corrosion rate of the degradable corrosion-resistant high strength and ductility magnesium alloy for biomedical use in artificial plasma was 0.26 mm/year, in a uniform corrosion manner. Biological test results showed that the material had no obvious cytotoxicity and good blood compatibility, which met the requirements for intravascular stent materials.

Example 2

This example provides a degradable corrosion-resistant high strength and ductility magnesium alloy for biomedical use. The composition of the magnesium alloy comprises, with regard to a total weight of the magnesium alloy of 100%, 2.0% of Nd, 0.6% of Zn, 0.5% of Ca, 0.6% of Zr, and balance of Mg.

The magnesium alloy was prepared by the following steps:

(1) In a vacuum melting furnace, pure magnesium having a purity of 99.99 wt % or more, pure Zn having a purity of 99.99 wt % or more, pure Ca having a purity of 99.99 wt % or more, a Mg-30 wt % Nd master alloy and a Mg-30 wt % Zr master alloy were successively melted, and the melt temperature during melting was controlled at 740 to 760° C. After the raw materials were completely melted, argon gas was introduced to conduct gas stirring in a vacuum environment with a stirring time of 40 min.

(2) After the stirring was completed, a mixed gas of $SF_6$ and $CO_2$ (volume ratio of $SF_6:CO_2$ in this mixed gas being 1:100) was introduced to the surface of the melt for protection, and at the same time, the temperature of the melt was raised to 760 to 780° C. and kept for 30 min. After the high temperature insulation, the melting furnace was powered off, and the temperature of the melt was controlled at 700 to 720° C. and the melt was allowed to stand for 90 min.

(3) Subsequently, a copper crystallizer was used for the ingot casting on a semi-continuous casting machine. The magnesium alloy melt was introduced into a diverter plate placed in the core of the inner sleeve of the crystallizer, and was diverted by the diverter plate into the space formed by the metal inner sleeve and the dummy bar of the crystallizer. At the same time, the protective gas ring was opened to provide a mixed gas of $SF_6$ and $CO_2$ (volume ratio of $SF_6:CO_2$ in this mixed gas being 1:100) to the alloy melt for protection. During the semi-continuous casting process, the temperature of the melt in the vacuum melting furnace was controlled at 700 to 720° C., the temperature of the melt in the crystallizer was 680 to 690° C., and the speed of ingot-drawing was 40 mm/min. High pressure water-cooling was applied at 400 mm close to the crystallizer, and air-cooling was applied at a lower region.

(4) The Mg—Nd—Zn—Ca—Zr magnesium alloy semi-continuous ingot obtained from the casting had a size of Φ120×2400 mm. The ingot had an appearance free of cracks and shrinkage, with a smooth and clean surface, fine and uniform structures, and no solute segregation.

(5) The resultant Mg—Nd—Zn—Ca—Zr magnesium alloy ingot was cut to a certain length, subjected to solid solution treatment at 520° C. for 10 hours, and then extruded at 330° C. to form a round rod having a diameter of Φ25 mm, and thus the degradable corrosion-resistant high strength and ductility magnesium alloy for biomedical use was obtained.

The degradable corrosion-resistant high strength and ductility magnesium alloy for biomedical use had a tensile strength of 277 MPa, a yield strength of 224 MPa and an elongation of 28%, as well as good plasticity and mechanical properties. The corrosion rate of the degradable corrosion-resistant high strength and ductility magnesium alloy for biomedical use in artificial plasma was 0.24 mm/year, in a uniform corrosion manner. Biological test results showed that the material had no obvious cytotoxicity and good blood compatibility, which met the requirements for intravascular stent materials.

Example 3

This example provides a degradable corrosion-resistant high strength and ductility magnesium alloy for biomedical use. The composition of the magnesium alloy comprises, with regard to a total weight of the magnesium alloy of 100%, 2.5% of Nd, 0.8% of Zn, 0.6% of Ca, 0.8% of Zr, and balance of Mg.

The magnesium alloy was prepared by the following steps:

(1) In a vacuum melting furnace, pure magnesium having a purity of 99.99 wt % or more, pure Zn having a purity of 99.99 wt % or more, pure Ca having a purity of 99.99 wt % or more, a Mg-30 wt % Nd master alloy and a Mg-30 wt % Zr master alloy were successively melted, and the melt temperature during melting was controlled at 740 to 760° C. After the raw materials were completely melted, argon gas was introduced to conduct gas stirring in a vacuum environment with a stirring time of 40 min.

(2) After the stirring was completed, a mixed gas of $SF_6$ and $CO_2$ (volume ratio of $SF_6$:$CO_2$ in this mixed gas being 1:100) was introduced to the surface of the melt for protection, and at the same time, the temperature of the melt was raised to 760 to 780° C. and kept for 30 to 40 min. After the high temperature insulation, the melting furnace was powered off, and the temperature of the melt was controlled at 700 to 720° C. and the melt was allowed to stand for 90 min.

(3) Subsequently, a copper crystallizer was used for the ingot casting on a semi-continuous casting machine. The magnesium alloy melt was introduced into a diverter plate placed in the core of the inner sleeve of the crystallizer, and was diverted by the diverter plate into the space formed by the metal inner sleeve and the dummy bar of the crystallizer. At the same time, the protective gas ring was opened to provide a mixed gas of $SF_6$ and $CO_2$ (volume ratio of $SF_6$:$CO_2$ in this mixed gas being 1:100) to the alloy melt for protection. During the semi-continuous casting process, the temperature of the melt in the vacuum melting furnace was controlled to 700 to 720° C., the temperature of the melt in the crystallizer was 680 to 690° C., and the speed of ingot-drawing was 40 mm/min. High pressure water-cooling was applied at 400 mm close to the crystallizer, and air-cooling was applied at a lower region.

(4) The Mg—Nd—Zn—Ca—Zr magnesium alloy semi-continuous ingot obtained from the casting had a size of Φ120×2400 mm. The ingot had an appearance free of cracks and shrinkage, with a smooth and clean surface, fine and uniform structures, and no solute segregation.

(5) The resultant Mg—Nd—Zn—Ca—Zr magnesium alloy ingot was cut to a certain length, subjected to solid solution treatment at 520° C. for 10 hours, and then extruded at 330° C. to form a round rod having a diameter of Φ25 mm, and thus the degradable corrosion-resistant high strength and ductility magnesium alloy for biomedical use was obtained.

The degradable corrosion-resistant high strength and ductility magnesium alloy for biomedical use had a tensile strength of 289 MPa, a yield strength of 232 MPa and an elongation of 25%, as well as good plasticity and mechanical properties. The corrosion rate of the degradable corrosion-resistant high strength and ductility magnesium alloy for biomedical use in artificial plasma was 0.22 mm/year, in a uniform corrosion manner. Biological test results showed that the material had no obvious cytotoxicity and good blood compatibility, which met the requirements for intravascular stent materials.

Example 4

This example provides a degradable corrosion-resistant high strength and ductility magnesium alloy for biomedical use. The composition of the magnesium alloy comprises, with regard to a total weight of the magnesium alloy of 100%, 1.5% of Nd, 0.4% of Zn, 0.4% of Zr, and balance of Mg.

The magnesium alloy was prepared by the following steps:

(1) In a vacuum melting furnace, pure magnesium having a purity of 99.99 wt % or more, pure Zn having a purity of 99.99 wt % or more, a Mg-30 wt % Nd master alloy and a Mg-30 wt % Zr master alloy were successively melted, and the melt temperature during melting was controlled at 740 to 760° C. After the raw materials were completely melted, argon gas was introduced to conduct gas stirring in a vacuum environment with a stirring time of 40 min.

(2) After the stirring was completed, a mixed gas of $SF_6$ and $CO_2$ (volume ratio of $SF_6$:$CO_2$ in this mixed gas being 1:100) was introduced to the surface of the melt for protection, and at the same time, the temperature of the melt was raised to 760 to 780° C. and kept for 30 min. After the high temperature insulation, the melting furnace was powered off, and the temperature of the melt was controlled at 700 to 720° C. and the melt was allowed to stand for 90 min.

(3) Subsequently, a copper crystallizer was used for the ingot casting on a semi-continuous casting machine. The magnesium alloy melt was introduced into a diverter plate placed in the core of the inner sleeve of the crystallizer, and was diverted by the diverter plate into the space formed by the metal inner sleeve and the dummy bar of the crystallizer. At the same time, the protective gas ring was opened to provide a mixed gas of $SF_6$ and $CO_2$ (volume ratio of $SF_6$:$CO_2$ in this mixed gas being 1:100) to the alloy melt for protection. During the semi-continuous casting process, the temperature of the melt in the vacuum melting furnace was controlled at 700 to 720° C., the temperature of the melt in the crystallizer was 680 to 690° C., and the speed of ingot-drawing was 40 mm/min. High pressure water-cooling was applied at 400 mm close to the crystallizer, and air-cooling was applied at a lower region.

(4) The Mg—Nd—Zn—Zr magnesium alloy semi-continuous ingot obtained from the casting had a size of Φ120×2400 mm. The ingot had an appearance free of cracks and shrinkage, with a smooth and clean surface, fine and uniform structures, and no solute segregation.

(5) The resultant Mg—Nd—Zn—Zr magnesium alloy ingot was cut to a certain length, subjected to solid solution treatment at 520° C. for 10 hours, and then extruded at 330° C. to form a round rod having a diameter of Φ25 mm, and thus the degradable corrosion-resistant high strength and ductility magnesium alloy for biomedical use was obtained.

The degradable corrosion-resistant high strength and ductility magnesium alloy for biomedical use had a tensile strength of 223 MPa, a yield strength of 188 MPa and an elongation of 24%. The corrosion rate of the degradable corrosion-resistant high strength and ductility magnesium alloy for biomedical use in artificial plasma was 0.32 mm/year. Biological test results showed that the material had no obvious cytotoxicity and good blood compatibility, which met the requirements for the biocompatibility of intravascular stent materials.

Example 5

This example provides a degradable corrosion-resistant high strength and ductility magnesium alloy for biomedical use. The composition of the magnesium alloy comprises, with regard to a total weight of the magnesium alloy of 100%, 1.5% of Nd, 0.4% of Zn, 0.4% of Ca, and balance of Mg.

The magnesium alloy was prepared by the following steps:

(1) In a vacuum melting furnace, pure magnesium having a purity of 99.99 wt % or more, pure Zn having a purity of 99.99 wt % or more, pure Ca having a purity of 99.99 wt % or more, and a Mg-30 wt % Zr master alloy were successively melted, and the melt temperature during melting was controlled at 740 to 760° C. After the raw materials were completely melted, argon gas was introduced to conduct gas stirring in a vacuum environment with a stirring time of 40 min.

(2) After the stirring was completed, a mixed gas of $SF_6$ and $CO_2$ (volume ratio of $SF_6:CO_2$ in this mixed gas being 1:100) was introduced to the surface of the melt for protection, and at the same time, the temperature of the melt was raised to 760 to 780° C. and kept for 30 min. After the high temperature insulation, the melting furnace was powered off, and the temperature of the melt was controlled at 700 to 720° C. and the melt was allowed to stand for 90 min.

(3) Subsequently, a copper crystallizer was used for the ingot casting on a semi-continuous casting machine. The magnesium alloy melt was introduced into a diverter plate placed in the core of the inner sleeve of the crystallizer, and was diverted by the diverter plate into the space formed by the metal inner sleeve and the dummy bar of the crystallizer. At the same time, the protective gas ring was opened to provide a mixed gas of $SF_6$ and $CO_2$ (volume ratio of $SF_6:CO_2$ in this mixed gas being 1:100) to the alloy melt for protection. During the semi-continuous casting process, the temperature of the melt in the vacuum melting furnace was controlled at 700 to 720° C., the temperature of the melt in the crystallizer was 680 to 690° C., and the speed of ingot-drawing was 40 mm/min. High pressure water-cooling was applied at 400 mm close to the crystallizer, and air-cooling was applied at a lower region.

(4) The Mg—Nd—Zn—Ca magnesium alloy semi-continuous ingot obtained from the casting had a size of Φ120×2400 mm. The ingot had an appearance free of cracks and shrinkage, with a smooth and clean surface, fine and uniform structures, and no solute segregation.

(5) The resultant Mg—Nd—Zn—Ca magnesium alloy ingot was cut to a certain length, subjected to solid solution treatment at 520° C. for 10 hours, and then extruded at 330° C. to form a round rod having a diameter of Φ25 mm, and thus the degradable corrosion-resistant high strength and ductility magnesium alloy for biomedical use was obtained.

The degradable corrosion-resistant high strength and ductility magnesium alloy for biomedical use had a tensile strength of 228 MPa, a yield strength of 196 MPa and an elongation of 21%. The corrosion rate of the degradable corrosion-resistant high strength and ductility magnesium alloy for biomedical use in artificial plasma was 0.36 mm/year. Biological test results showed that the material had no obvious cytotoxicity and good blood compatibility, which met the requirements for the biocompatibility of intravascular stent materials.

Example 6

This example provides a degradable corrosion-resistant high strength and ductility magnesium alloy for biomedical use. The composition of the magnesium alloy comprises, with regard to a total weight of the magnesium alloy of 100%, 1.5% of Nd, 2.0% of Zn, 0.4% of Ca, 0.4% of Zr, and balance of Mg.

The magnesium alloy was prepared by the following steps:

(1) In a vacuum melting furnace, pure magnesium having a purity of 99.99 wt % or more, pure Zn having a purity of 99.99 wt % or more, pure Ca having a purity of 99.99 wt % or more, a Mg-30 wt % Nd master alloy and a Mg-30 wt % Zr master alloy were successively melted, and the melt temperature during melting was controlled at 740 to 760° C. After the raw materials were completely melted, argon gas was introduced to conduct gas stirring in a vacuum environment with a stirring time of 40 min.

(2) After the stirring was completed, a mixed gas of $SF_6$ and $CO_2$ (volume ratio of $SF_6:CO_2$ in this mixed gas being 1:100) was introduced to the surface of the melt for protection, and at the same time, the temperature of the melt was raised to 760 to 780° C. and kept for 30 min. After the high temperature insulation, the melting furnace was powered off, and the temperature of the melt was controlled at 700 to 720° C. and the melt was allowed to stand for 90 min.

(3) Subsequently, a copper crystallizer was used for the ingot casting on a semi-continuous casting machine. The magnesium alloy melt was introduced into a diverter plate placed in the core of the inner sleeve of the crystallizer, and was diverted by the diverter plate into the space formed by the metal inner sleeve and the dummy bar of the crystallizer. At the same time, the protective gas ring was opened to provide a mixed gas of $SF_6$ and $CO_2$ (volume ratio of $SF_6:CO_2$ in this mixed gas being 1:100) to the alloy melt for protection. During the semi-continuous casting process, the temperature of the melt in the vacuum melting furnace was controlled at 700 to 720° C., the temperature of the melt in the crystallizer was 680 to 690° C., and the speed of ingot-drawing was 40 mm/min. High pressure water-cooling was applied at 400 mm close to the crystallizer, and air-cooling was applied at a lower region.

(4) The Mg—Nd—Zn—Ca—Zr magnesium alloy semi-continuous ingot obtained from the casting had a size of Φ120×2400 mm. The ingot had an appearance free of cracks and shrinkage, with a smooth and clean surface, fine and uniform structures, and no solute segregation.

(5) The resultant Mg—Nd—Zn—Ca—Zr magnesium alloy ingot was cut to a certain length, subjected to solid solution treatment at 520° C. for 10 hours, and then extruded at 330° C. to form a round rod having a diameter of Φ25 mm, and thus the degradable corrosion-resistant high strength and ductility magnesium alloy for biomedical use was obtained.

The degradable corrosion-resistant high strength and ductility magnesium alloy for biomedical use had a tensile strength of 256 MPa, a yield strength of 219 MPa and an elongation of 18%. The corrosion rate of the degradable corrosion-resistant high strength and ductility magnesium alloy for biomedical use in artificial plasma was 0.44 mm/year. Biological test results showed that the material had no obvious cytotoxicity and good blood compatibility, which met the requirements for the biocompatibility of intravascular stent materials.

Comparative Example 1

This comparative example provides a biomedical magnesium alloy. The composition of the magnesium alloy comprises, with regard to a total weight of the magnesium alloy of 100%, 1.5% of Y, 0.4% of Zn, 0.4% of Zr, and balance of Mg.

The magnesium alloy was prepared by the following steps:

(1) In a vacuum melting furnace, pure magnesium having a purity of 99.99 wt % or more, pure Zn having a purity of 99.99 wt % or more, a Mg-30 wt % Y master alloy and a Mg-30 wt % Zr master alloy were successively melted, and the melt temperature during melting was controlled at 740 to 760° C. After the raw materials were completely melted, argon gas was introduced to conduct gas stirring in a vacuum environment with a stirring time of 40 min.

(2) After the stirring was completed, a mixed gas of $SF_6$ and $CO_2$ (volume ratio of $SF_6:CO_2$ in this mixed gas being 1:100) was introduced to the surface of the melt for protection, and at the same time, the temperature of the melt was raised to 760 to 780° C. and kept for 30 min. After the high temperature insulation, the melting furnace was powered off, and the temperature of the melt was controlled at 700 to 720° C. and the melt was allowed to stand for 90 min.

(3) Subsequently, a copper crystallizer was used for the ingot casting on a semi-continuous casting machine. The magnesium alloy melt was introduced into a diverter plate placed in the core of the inner sleeve of the crystallizer, and was diverted by the diverter plate into the space formed by the metal inner sleeve and the dummy bar of the crystallizer. At the same time, the protective gas ring was opened to provide a mixed gas of $SF_6$ and $CO_2$ (volume ratio of $SF_6:CO_2$ in this mixed gas being 1:100) to the alloy melt for protection. During the semi-continuous casting process, the temperature of the melt in the vacuum melting furnace was controlled at 700 to 720° C., the temperature of the melt in the crystallizer was 680 to 690° C., and the speed of ingot-drawing was 40 mm/min. High pressure water-cooling was applied at 400 mm close to the crystallizer, and air-cooling was applied at a lower region.

(4) The Mg—Y—Zn—Zr magnesium alloy semi-continuous ingot obtained from the casting had a size of Φ120×2400 mm. The ingot had an appearance free of cracks and shrinkage, with a smooth and clean surface, fine and uniform structures, and no solute segregation.

(5) The resultant Mg—Y—Zn—Zr magnesium alloy ingot was cut to a certain length, subjected to solid solution treatment at 520° C. for 10 hours, and then extruded at 330° C. to form a round rod having a diameter of Φ25 mm, and thus the biomedical corrosion resistant high strength and toughness magnesium alloy was obtained.

The biomedical magnesium alloy had a tensile strength of 216 MPa, a yield strength of 176 MPa and an elongation of 19%. The corrosion rate of the biomedical magnesium alloy in artificial plasma was 0.37 mm/year.

Comparative Example 2

This comparative example provides a biomedical magnesium alloy. The composition of the magnesium alloy comprises, with regard to a total weight of the magnesium alloy of 100%, 1.5% of Y, 0.4% of Zn, 0.4% of Ca, and balance of Mg.

The magnesium alloy was prepared by the following steps:

(1) In a vacuum melting furnace, pure magnesium having a purity of 99.99 wt % or more, pure Zn having a purity of 99.99 wt % or more, pure Ca having a purity of 99.99 wt % or more, and a Mg-30 wt % Y master alloy were successively melted, and the melt temperature during melting was controlled at 740 to 760° C. After the raw materials were completely melted, argon gas was introduced to conduct gas stirring in a vacuum environment with a stirring time of 40 min.

(2) After the stirring was completed, a mixed gas of $SF_6$ and $CO_2$ (volume ratio of $SF_6:CO_2$ in this mixed gas being 1:100) was introduced to the surface of the melt for protection, and at the same time, the temperature of the melt was raised to 760 to 780° C. and kept for 30 min. After the high temperature insulation, the melting furnace was powered off, and the temperature of the melt was controlled at 700 to 720° C. and the melt was allowed to stand for 90 min.

(3) Subsequently, a copper crystallizer was used for the ingot casting on a semi-continuous casting machine. The magnesium alloy melt was introduced into a diverter plate placed in the core of the inner sleeve of the crystallizer, and was diverted by the diverter plate into the space formed by the metal inner sleeve and the dummy bar of the crystallizer. At the same time, the protective gas ring was opened to provide a mixed gas of $SF_6$ and $CO_2$ (volume ratio of $SF_6:CO_2$ in this mixed gas being 1:100) to the alloy melt for protection. During the semi-continuous casting process, the temperature of the melt in the vacuum melting furnace was controlled at 700 to 720° C., the temperature of the melt in the crystallizer was 680 to 690° C., and the speed of ingot-drawing was 40 mm/min. High pressure water-cooling was applied at 400 mm close to the crystallizer, and air-cooling was applied at a lower region.

(4) The Mg—Y—Zn—Ca magnesium alloy semi-continuous ingot obtained from the casting had a size of Φ120×2400 mm. The ingot had an appearance free of cracks and shrinkage, with a smooth and clean surface, fine and uniform structures, and no solute segregation.

(5) The resultant Mg—Y—Zn—Ca magnesium alloy ingot was cut to a certain length, subjected to solid solution treatment at 520° C. for 10 hours, and then extruded at 330° C. to form a round rod having a diameter of Φ25 mm, and thus the biomedical magnesium alloy was obtained.

The biomedical magnesium alloy had a tensile strength of 213 MPa, a yield strength of 172 MPa and an elongation of 22%. The corrosion rate of the biomedical magnesium alloy in artificial plasma was 0.43 mm/year.

Comparative Example 3

This comparative example provides a biomedical magnesium alloy. The composition of the magnesium alloy comprises, with regard to a total weight of the magnesium alloy of 100%, 1.5% of Y, 2.0% of Zn, 0.4% of Ca, and balance of Mg.

The magnesium alloy was prepared by the following steps:

(1) In a vacuum melting furnace, pure magnesium having a purity of 99.99 wt % or more, pure Zn having a purity of 99.99 wt % or more, pure Ca having a purity of 99.99 wt % or more, a Mg-30 wt % Y master alloy and a Mg-30 wt % Zr master alloy were successively melted, and the melt temperature during melting was controlled at 740 to 760° C. After the raw materials were completely melted, argon gas was introduced to conduct gas stirring in a vacuum environment with a stirring time of 40 min.

(2) After the stirring was completed, a mixed gas of $SF_6$ and $CO_2$ (volume ratio of $SF_6$:$CO_2$ in this mixed gas being 1:100) was introduced to the surface of the melt for protection, and at the same time, the temperature of the melt was raised to 760 to 780° C. and kept for 30 min. After the high temperature insulation, the melting furnace was powered off, and the temperature of the melt was controlled at 700 to 720° C. and the melt was allowed to stand for 90 min.

(3) Subsequently, a copper crystallizer was used for the ingot casting on a semi-continuous casting machine. The magnesium alloy melt was introduced into a diverter plate placed in the core of the inner sleeve of the crystallizer, and was diverted by the diverter plate into the space formed by the metal inner sleeve and the dummy bar of the crystallizer. At the same time, the protective gas ring was opened to provide a mixed gas of $SF_6$ and $CO_2$ (volume ratio of $SF_6$:$CO_2$ in this mixed gas being 1:100) to the alloy melt for protection. During the semi-continuous casting process, the temperature of the melt in the vacuum melting furnace was controlled at 700 to 720° C., the temperature of the melt in the crystallizer was 680 to 690° C., and the speed of ingot-drawing was 40 mm/min. High pressure water-cooling was applied at 400 mm close to the crystallizer, and air-cooling was applied at a lower region.

(4) The Mg—Y—Zn—Ca—Zr magnesium alloy semi-continuous ingot obtained from the casting had a size of Φ120×2400 mm. The ingot had an appearance free of cracks and shrinkage, with a smooth and clean surface, fine and uniform structures, and no solute segregation.

(5) The resultant Mg—Y—Zn—Ca—Zr magnesium alloy ingot was cut to a certain length, subjected to solid solution treatment at 520° C. for 10 hours, and then extruded at 330° C. to form a round rod having a diameter of Φ25 mm, and thus the biomedical magnesium alloy was obtained.

The biomedical magnesium alloy had a tensile strength of 236 MPa, a yield strength of 204 MPa and an elongation of 17%. The corrosion rate of the biomedical magnesium alloy in artificial plasma was 0.48 mm/year.

TABLE 1

Magnesium alloy composition and related properties

| Example No. | Composition (wt %) | Tensile strength (MPa) | Yield Strength (MPa) | Elongation (%) | Corrosion rate (mm/year) | Corrosion mode |
|---|---|---|---|---|---|---|
| Example 1 | Mg—1.5Nd—0.4Zn—0.4Ca—0.4Zr | 246 | 207 | 34 | 0.26 | Uniform corrosion |
| Example 2 | Mg—2.0Nd—0.6Zn—0.5Ca—0.6Zr | 277 | 224 | 28 | 0.24 | Uniform corrosion |
| Example 3 | Mg—2.5Nd—0.8Zn—0.6Ca—0.8Zr | 289 | 232 | 25 | 0.22 | Uniform corrosion |
| Example 4 | Mg—1.5Nd—0.4Zn—0.4Zr | 223 | 188 | 24 | 0.32 | — |
| Example 5 | Mg—1.5Nd—0.4Zn—0.4Ca | 228 | 196 | 21 | 0.36 | — |
| Example 6 | Mg—1.5Nd—2.0Zn—0.4Ca—0.4Zr | 256 | 219 | 18 | 0.44 | — |
| Comparative Example 1 | Mg—1.5Y—0.4Zn—0.4Zr | 216 | 176 | 19 | 0.37 | — |
| Comparative Example 2 | Mg—1.5Y—0.4Zn—0.4Ca | 213 | 172 | 22 | 0.43 | — |
| Comparative Example 3 | Mg—1.5Y—2.0Zn—0.4Ca—0.4Zr | 236 | 204 | 17 | 0.48 | — |

As can be seen from Table 1, the magnesium alloy prepared by implementing the most preferred embodiments of the present disclosure has a tensile strength of 246 to 289 MPa, a yield strength of 207 to 232 MPa and an elongation rate of up to 25 to 34%, which meets the requirements for the mechanical properties of intravascular stent materials. Its corrosion rate in artificial plasma can reach 0.22 to 0.26 mm/year, which meets the requirement for the corrosion resistance of intravascular stent materials. In addition, the magnesium alloy has no obvious cytotoxicity and good blood compatibility, which meets the requirements for the biocompatibility of intravascular stent materials.

The invention claimed is:

1. A degradable corrosion-resistant strength and ductility magnesium alloy for biomedical use, wherein the composition of components of the magnesium alloy consists of 1.5 to 2.5% of Nd, 0.4 to 0.8% of Zn, 0.4 to 0.6% of Ca, 0.4 to 0.8% of Zr, and balance of Mg, with regard to a total weight of the magnesium alloy of 100%.

2. The degradable corrosion-resistant strength and ductility magnesium alloy for biomedical use according to claim 1, which is prepared by at least the step of: preparing a magnesium alloy ingot by means of vacuum semi-continuous casting and according to the components and weight percentage in the degradable corrosion-resistant strength and ductility magnesium alloy for biomedical use, wherein the raw materials used comprise at least: pure Zn, a Mg—Nd master alloy, and pure magnesium.

3. The degradable corrosion-resistant strength and ductility magnesium alloy for biomedical use according to claim 2, wherein the raw materials used further comprise pure Ca and/or a Mg—Zr master alloy.

4. The degradable corrosion-resistant strength and ductility magnesium alloy for biomedical use according to claim 3, wherein the pure Ca used has a purity of 99.99 wt % or more, and the Mg—Zr master alloy used is a Mg—30 wt % Zr master alloy.

5. The degradable corrosion-resistant strength and ductility magnesium alloy for biomedical use according to claim 2, wherein the pure Zn used has a purity of 99.99 wt % or more, the Mg—Nd master alloy used is a Mg-30 wt % Nd master alloy, and the pure magnesium used has a purity of 99.99 wt % or more.

6. The degradable corrosion-resistant strength and ductility magnesium alloy for biomedical use according to claim 2, wherein the resultant magnesium alloy ingot has a size of Φ110 to 150 mm in diameter and 2200 to 2600 mm in length.

7. The degradable corrosion-resistant strength and ductility magnesium alloy for biomedical use according to claim 2, wherein the preparation of the degradable corrosion-resistant strength and ductility magnesium alloy for biomedical use further comprises: cutting the resultant magnesium alloy ingot to a certain length, and subjecting it to solid solution treatment before extruding, so as to obtain the degradable corrosion-resistant strength and ductility magnesium alloy for biomedical use.

8. The degradable corrosion-resistant strength and ductility magnesium alloy for biomedical use according to claim 7, wherein the temperature for the solid solution treatment is 480 to 540° C., the duration of the solid solution treatment is 8 to 12 hours, the extrusion is performed at an extruding ratio of 5 to 30 in an environment at 280 to 420° C., and the degradable corrosion-resistant high strength and ductility magnesium alloy for biomedical use is obtained after the extrusion as a round rod with a diameter of Φ20 to 40 mm.

9. A preparation method for the degradable corrosion-resistant high strength and ductility magnesium alloy for biomedical use according to claim 1, comprising at least the step of: preparing a magnesium alloy ingot by means of vacuum semi-continuous casting and according to the components and weight percentage in the degradable corrosion-resistant strength and ductility magnesium alloy for biomedical use, wherein the raw materials used comprise at least: pure Zn, a Mg—Nd master alloy, and pure magnesium.

10. The preparation method according to claim 9, wherein the raw materials used further comprise pure Ca and/or a Mg—Zr master alloy.

11. The preparation method according to claim 10, wherein the pure Ca used has a purity of 99.99 wt % or more, and the Mg—Zr master alloy used is a Mg-30 wt % Zr master alloy.

12. The preparation method according to claim 9, wherein the pure Zn used has a purity of 99.99 wt % or more, the Mg—Nd master alloy used is a Mg-30 wt % Nd master alloy, and the pure magnesium used has a purity of 99.99 wt % or more.

13. The preparation method according to claim 9, wherein the vacuum semi-continuous casting comprises the following steps:
(1) the raw materials are melted in a vacuum melting furnace with a melt temperature controlled at 740 to 760° C. during melting, and after the raw materials are completely melted, an inert gas is introduced for stirring by gas in a vacuum environment with a stirring time of 30 to 45 min;
(2) after the stirring is completed, a mixed gas of $SF_6$ and $CO_2$ is introduced to the surface of the melt for protection while the temperature of the melt is raised to 760 to 780° C. and kept for 30 to 40 min, and then the temperature of the melt is lowered to 700 to 720° C. and the melt is allowed to stand for 90 to 120 min;
(3) casting is then carried out on a semi-continuous casting machine; during the semi-continuous casting process, a gas mixture of $SF_6$ and $CO_2$ is used for protection, the temperature of the melt in the vacuum melting furnace is controlled at 700 to 720° C., with the temperature of the melt in a crystallizer at 680 to 690° C. and a speed of ingot-drawing of 30 to 50 mm/min, and pressure water-cooling is applied at 300 to 500 mm close to the crystallizer while air-cooling is applied at a lower region, thereby obtaining the magnesium alloy ingot.

14. The preparation method according to claim 9, wherein the resultant magnesium alloy ingot has a size of Φ110 to 150 mm in diameter and 2200 to 2600 mm in length.

15. The preparation method according to claim 9, further comprising the following steps: cutting the obtained magnesium alloy ingot to a certain length, and subjecting it to solid solution treatment before extruding, so as to obtain the degradable corrosion-resistant strength and ductility magnesium alloy for biomedical use.

16. The preparation method according to claim 15, wherein the temperature for the solid solution treatment is 480 to 540° C., the duration of the solid solution treatment is 8 to 12 hours, the extrusion is performed at an extruding ratio of 5 to 30 in an environment at 280 to 420° C., and the degradable corrosion-resistant strength and ductility magnesium alloy for biomedical use is obtained after the extrusion as a round rod with a diameter of Φ20 to 40 mm.

17. A degradable corrosion-resistant strength and ductility magnesium alloy for biomedical use, wherein the composition of components of the magnesium alloy consist of 1.5 to 2.5% of Nd, 0.4 to 0.8% of Zn, 0.4 to 0.6% of Ca, 0.4 to 0.8% of Zr, inclusion elements other than Mg, Nd, Zn, Ca, and Zr, and balance of Mg, and the total amount of inclusion elements other than Mg, Nd, Zn, Ca, and Zr contained in the magnesium alloy is 0.05% or less, with regard to a total weight of the magnesium alloy of 100%.

* * * * *